(12) United States Patent
Fernandes et al.

(10) Patent No.: US 11,771,422 B2
(45) Date of Patent: Oct. 3, 2023

(54) ACTIVE ROLLER ASSEMBLY FOR USE IN ARTICULATING STAPLER

(71) Applicant: Covidien LP, Mansfield, MA (US)

(72) Inventors: Roanit A. Fernandes, Hyderabad (IN); Varad V. Chavan, Kolhapur (IN)

(73) Assignee: COVIDIEN LP, Mansfield, MA (US)

( * ) Notice: Subject to any disclaimer, the term of this patent is extended or adjusted under 35 U.S.C. 154(b) by 135 days.

(21) Appl. No.: 17/246,770

(22) Filed: May 3, 2021

(65) Prior Publication Data

US 2021/0353290 A1  Nov. 18, 2021

Related U.S. Application Data

(60) Provisional application No. 63/023,316, filed on May 12, 2020.

(51) Int. Cl.
*A61B 17/068* (2006.01)
*A61B 17/072* (2006.01)
*A61B 17/00* (2006.01)

(52) U.S. Cl.
CPC ........ *A61B 17/0686* (2013.01); *A61B 17/072* (2013.01); *A61B 2017/00367* (2013.01); *A61B 2017/07257* (2013.01); *A61B 2017/07271* (2013.01)

(58) Field of Classification Search
CPC .............. A61B 17/0686; A61B 17/072; A61B 17/07207; A61B 17/285; A61B 17/295; A61B 2017/07257; A61B 2017/07271; A61B 2017/07285; A61B 2017/2903; A61B 2017/2927; A61B 2017/2939; A61B 2017/294; A61B 2017/2943; A61B 2017/00367; A61B 2034/305;
(Continued)

(56) References Cited

U.S. PATENT DOCUMENTS 5,389,098 A * 2/1995 Tsuruta ............ A61B 17/07207
606/49
5,456,401 A 10/1995 Green et al.
(Continued)

FOREIGN PATENT DOCUMENTS

EP  1992296 A1  11/2008
EP  3545860 A2  10/2019
(Continued)

OTHER PUBLICATIONS

Extended European Search Report dated Octobers, 2021 corresponding to counterpart Patent Application EP 21173086.6.
(Continued)

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

A surgical stapler is described herein which includes a drive assembly. The drive assembly includes: a rotatable drive member defining a transverse axis; a linkage operably coupled to the rotatable drive member defining a longitudinal axis; and an I-beam operably coupled to the linkage, configured to be advanced along the longitudinal axis in response to a rotational motion of the rotatable drive member.

17 Claims, 9 Drawing Sheets

(58) Field of Classification Search
CPC ....... A61B 2034/306; F16H 2019/0613; F16H 55/26; F16H 19/04

See application file for complete search history.

(56) References Cited

U.S. PATENT DOCUMENTS

| | | | |
|---|---|---|---|
| 5,546,826 A * | 8/1996 | Yanagisawa | F16H 57/12 74/89.32 |
| 5,792,135 A | 8/1998 | Madhani et al. | |
| 5,865,361 A | 2/1999 | Milliman et al. | |
| 7,143,924 B2 | 12/2006 | Scirica et al. | |
| 7,159,750 B2 | 1/2007 | Racenet et al. | |
| 7,588,176 B2 | 9/2009 | Timm et al. | |
| 8,770,459 B2 | 7/2014 | Racenet et al. | |
| 9,700,309 B2 | 7/2017 | Jaworek | |
| 2005/0006432 A1 * | 1/2005 | Racenet | A61B 34/71 227/176.1 |
| 2008/0287977 A1 * | 11/2008 | Viola | A61B 17/07207 606/171 |
| 2008/0308607 A1 * | 12/2008 | Timm | A61B 17/07207 227/176.1 |
| 2009/0114699 A1 | 5/2009 | Viola | |
| 2013/0000428 A1 * | 1/2013 | Ji | A61N 5/1045 74/30 |
| 2016/0166253 A1 * | 6/2016 | Knodel | A61B 17/07207 227/175.1 |
| 2017/0042535 A1 | 2/2017 | Racenet et al. | |
| 2017/0265954 A1 | 9/2017 | Burbank et al. | |
| 2021/0177412 A1 * | 6/2021 | Wilson | A61B 17/07207 |

FOREIGN PATENT DOCUMENTS

| | | | |
|---|---|---|---|
| GB | 2188303 A * | 9/1987 | B25J 9/041 |
| WO | 2018049217 A1 | 3/2018 | |

OTHER PUBLICATIONS

European Office Action dated Jun. 27, 2023, issued in corresponding EP Appln. No. 21173086, 7 pages.

* cited by examiner

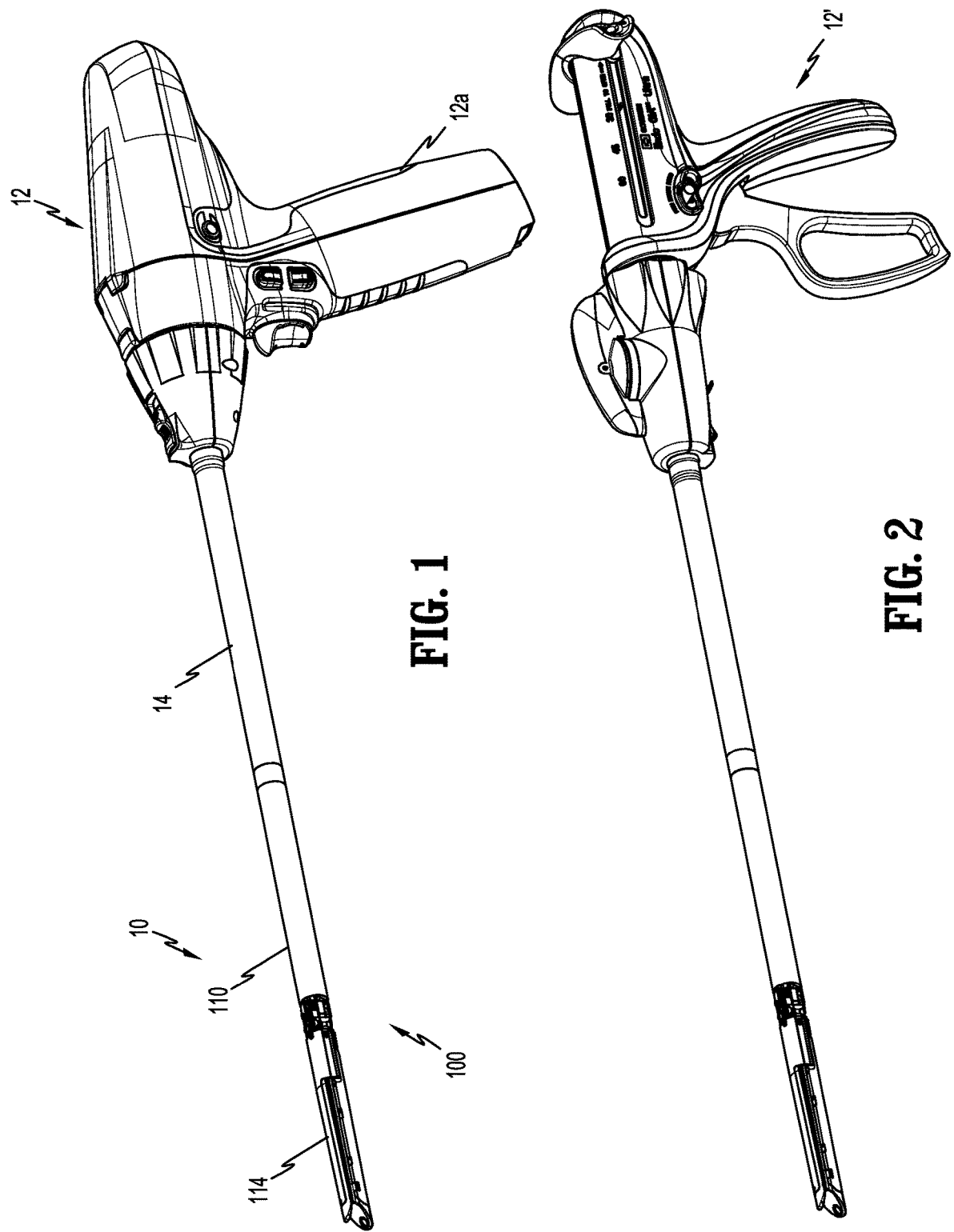

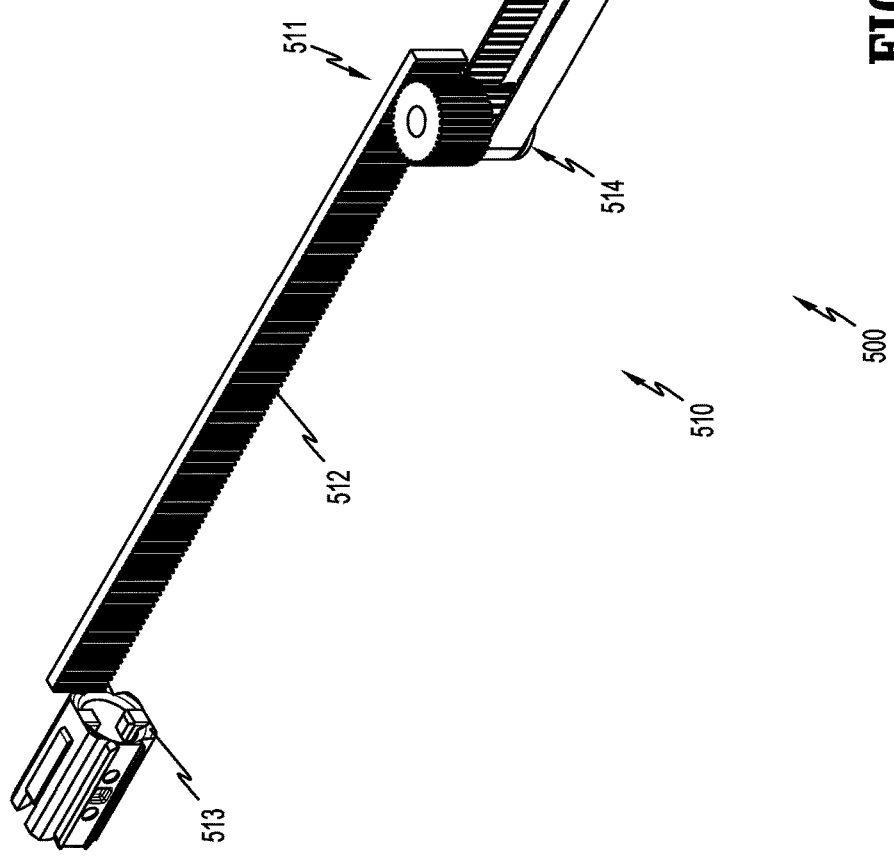
FIG. 5
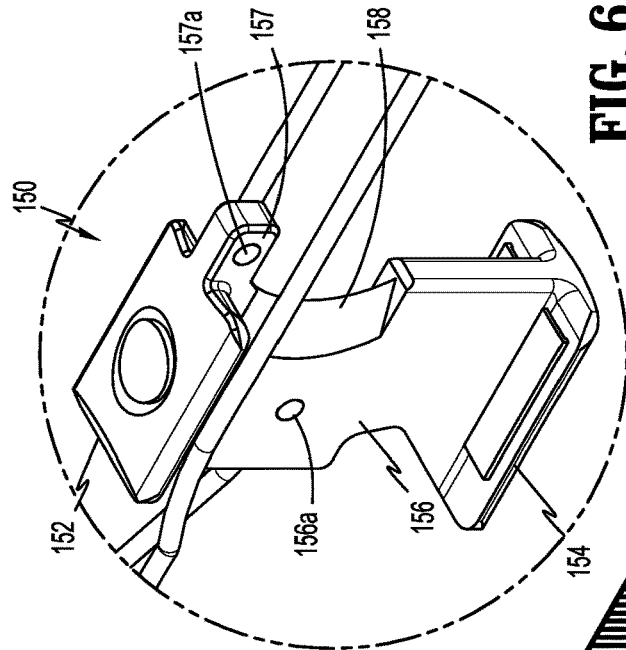
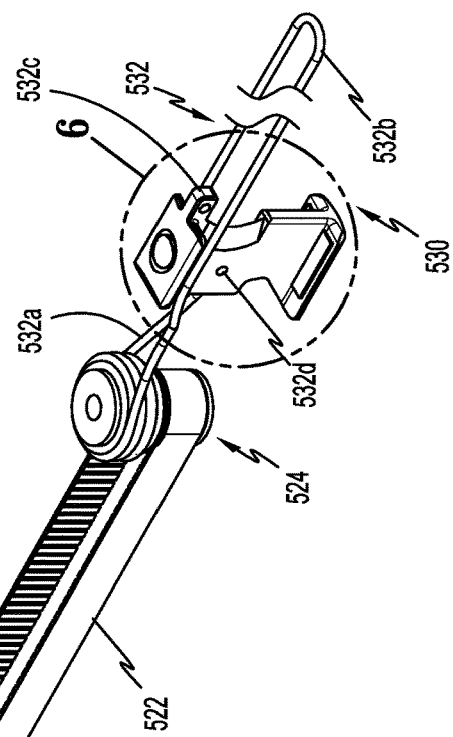
FIG. 6

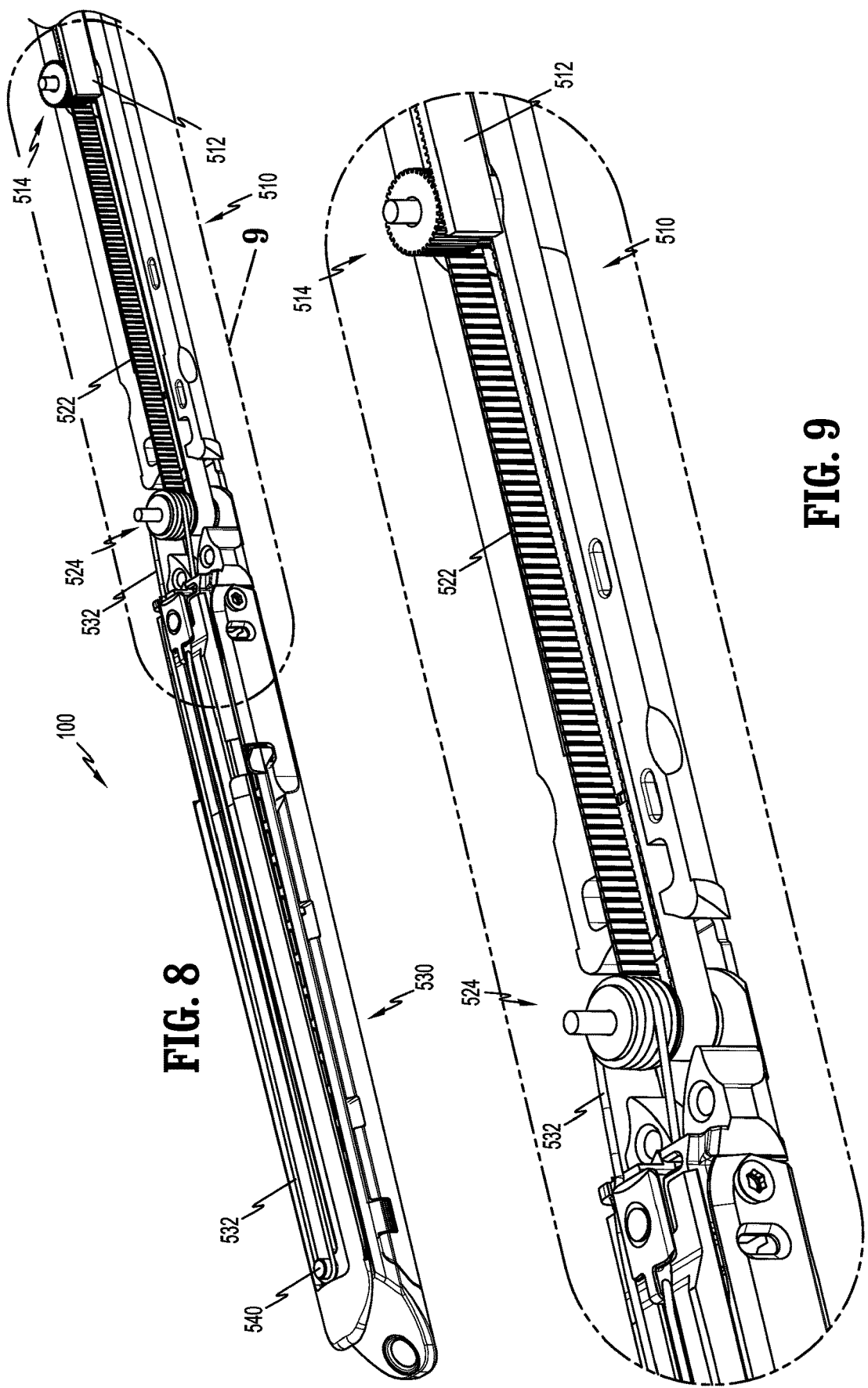

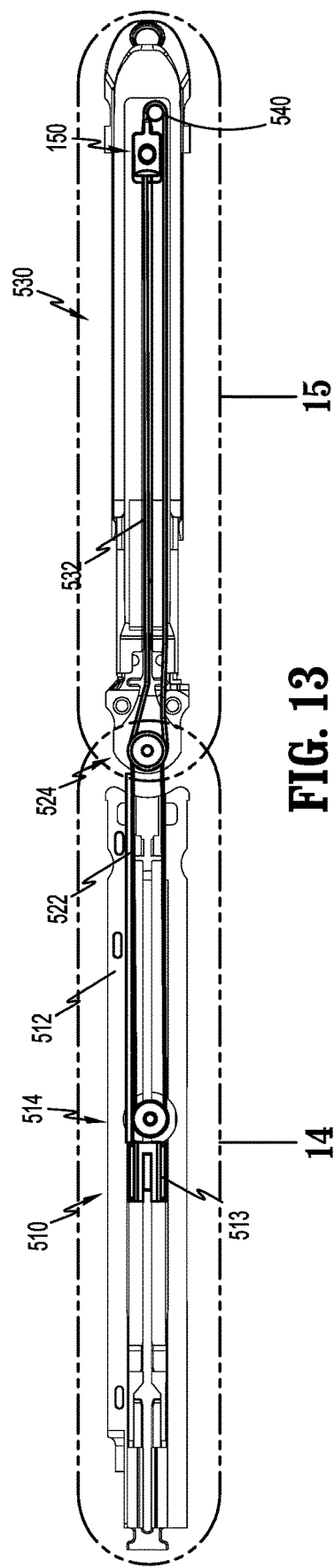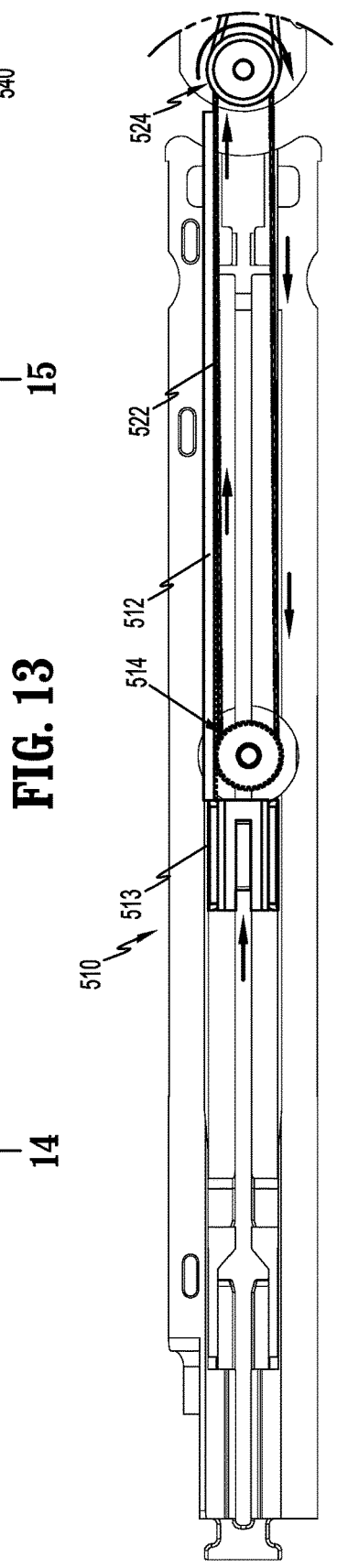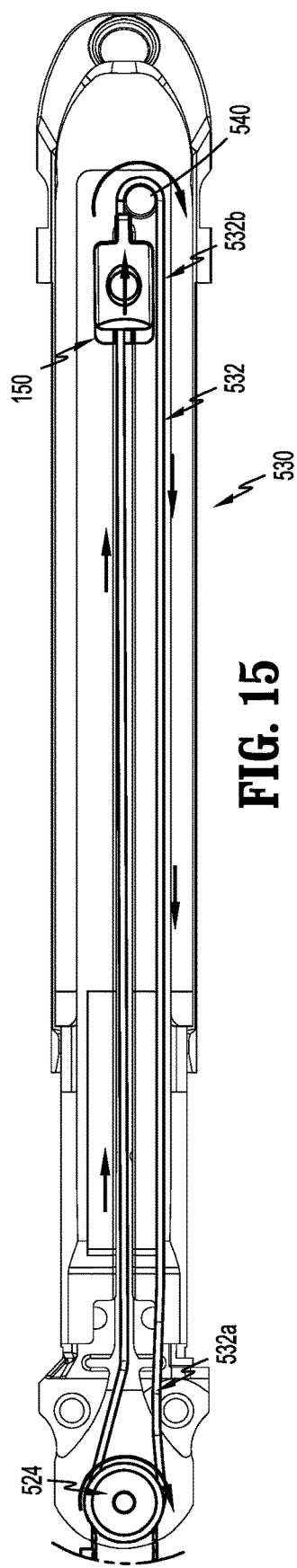

ACTIVE ROLLER ASSEMBLY FOR USE IN ARTICULATING STAPLER

CROSS-REFERENCE TO RELATED APPLICATION

The present application claims the benefit of and priority to U.S. Provisional Patent Application Ser. No. 63/023,316, filed on May 12, 2020, the entire content of which being hereby incorporated by reference.

BACKGROUND

Technical Field

This disclosure relates to surgical staplers, and more particularly, to surgical staplers with articulating tool assemblies.

Background

Surgical staplers typically include a tool assembly having a cartridge housing a plurality of staples, an anvil for forming the staples as the staples are ejected from the cartridge, and a knife to effect simultaneous dissection and suturing of tissue. When compared to applying manually threaded sutures during a surgical procedure, the use of surgical staplers to suture and dissect tissue has increased the speed of the surgical procedure and, thus, minimized patient trauma.

In an endoscopic surgical procedure, the tool assembly of the surgical stapler is inserted into a body cavity through a small incision in the skin or through a cannula to access a surgical site. In order to better access the surgical site after the tool assembly is positioned within the body cavity, the tool assembly of the surgical stapler is typically mounted to the surgical stapler for articulation. In this respect, the surgical stapler includes a mechanism for articulating the tool assembly. Due to space restrictions, the degree to which the tool assembly can be articulated with existing articulation mechanisms is limited.

A continuing need exists in the art for a surgical stapler suitable for endoscopic use that includes an articulation mechanism capable of articulating a tool assembly over a large range of motion within a body cavity during a surgical procedure.

SUMMARY

In accordance with aspects of the disclosure, a rotatable drive assembly is presented. The rotatable drive assembly includes a rotatable drive member defining a transverse axis; a linkage operably coupled to the rotatable drive member defining a longitudinal axis; and an I-beam operably coupled to the linkage. The I-beam is configured to be advanced along the longitudinal axis in response to rotational motion of the rotatable drive member.

In an aspect of the disclosure, the rotatable drive member may be configured to be driven by a motor.

In another aspect of the disclosure, the rotatable drive member may include a longitudinally movable rack gear and a pinion operably coupled to the rack gear. The longitudinal movement of the rack gear may impart rotational motion to the pinion.

In yet another aspect of the disclosure, the rack gear may be coupled to a coupling device, such that longitudinal movement of the coupling device may impart longitudinal movement of the rack gear.

In a further aspect of the disclosure, the pinion may be coupled to the linkage.

In yet a further aspect of the disclosure, the linkage may advance or retract the I-beam.

In an aspect of the disclosure, the linkage may include a pulley system.

In another aspect of the disclosure, the linkage may include a belt.

In yet another aspect of the disclosure, the linkage may include a metal wire and/or a synthetic wire.

In accordance with aspects of the disclosure, a surgical reload assembly is presented. The surgical reload assembly includes a tool assembly defining a longitudinal axis and a drive assembly. The tool assembly includes an anvil and a staple cartridge supporting a plurality of staples; and a drive assembly configured to eject staples from the surgical reload assembly. The drive assembly includes: a rotatable drive member defining a transverse axis; a linkage operably coupled to the rotatable drive member defining a longitudinal axis; and an I-beam operably coupled to the linkage. The I-beam is configured to be advanced, along the longitudinal axis in response to a rotational motion of the rotatable drive member, through the tool assembly to eject the plurality of staples from the staple cartridge.

In an aspect of the disclosure, the rotatable drive member may be configured to be driven by a motor.

In another aspect of the disclosure, the rotatable drive member may include a longitudinally moveable rack gear and a pinion operably coupled to the rack gear. The longitudinal movement of the rack gear may impart rotational motion to the pinion.

In yet another aspect of the disclosure, the rack gear may be configured to be operatively coupled to a coupling device, such that longitudinal movement of the coupling device may impart longitudinal movement of the rack gear.

In a further aspect of the disclosure, the pinion may be coupled to the linkage.

In yet a further aspect of the disclosure, the linkage may advance or retract the I-beam.

In an aspect of the disclosure, the linkage may include a pulley system.

In another aspect of the disclosure, the linkage may include a belt.

In yet another aspect of the disclosure, the linkage may include a metal wire and/or a synthetic wire.

In accordance with aspects of the disclosure, a surgical stapler is presented. The surgical stapler includes an actuating device, a reload assembly. The actuating device includes a firing trigger and an articulation lever. The reload assembly includes a tool assembly, and a drive assembly supported within the elongated body. The drive assembly configured to eject staples from the surgical reload assembly. The drive assembly includes a proximal drive train and a distal drive train operably coupled to the proximal drive train. The distal drive train includes an active roller, having a first portion and a second portion.

In yet a further aspect of the disclosure, the proximal drive train may include a push member, a rack assembly, and a linkage. The push member may include a proximal end and distal end. The rack assembly may include a rack gear and a rotatable drive member. The rotatable drive member operably coupled to the rack gear, the rotatable drive member including a pinion and an idle roller. The rack gear may be disposed on the distal end of the push member. The rack gear is configured to advance or retract in a longitudinal axis. The linkage may be operably coupled to the idle roller. The linkage may have a proximal portion and a distal portion. The distal portion of the linkage may be operably coupled to the first portion of the active roller. The rack gear may engage the pinion. The pinion may be configured to impart a clockwise rotation motion and/or a counterclockwise rotation motion to the idle roller. The proximal portion of the linkage is operably coupled to the idle roller. The distal portion of the linkage is operably coupled to the active roller.

BRIEF DESCRIPTION OF THE DRAWINGS

The accompanying drawings, which are incorporated in and constitute a part of this specification, illustrate aspects of the disclosure and, together with the detailed description of the aspects of the disclosure given below, serve to explain the principles of the disclosure. The figures depict various aspects of the disclosure for purposes of illustration only. One skilled in the art will readily recognize from the following discussion that alternative aspects of the structures and methods illustrated herein may be employed without departing from the principles of the disclosure described herein.

FIG. 1 is a side perspective view of exemplary aspects of a powered version of the disclosed surgical stapler in an unapproximated position;

FIG. 2 is a side perspective view of a manually operated version of the disclosed surgical stapler in an unapproximated position;

FIG. 5 is an enlarged view of the indicated area of detail shown in FIG. 4;

FIG. 6 is an enlarged view of the indicated area of detail shown in FIG. 5;

FIG. 8 is a side perspective view of the surgical stapler reload shown in FIG. 3 with a proximal body tube removed;

FIG. 9 is an enlarged view of the indicated area of detail shown in FIG. 8;

FIG. 13 is a top, functional view of the drive train of the surgical stapler reload shown in FIG. 1 in the non-articulated, fired position;

FIG. 14 is an enlarged view of the indicated area of detail shown in FIG. 13;

FIG. 15 is an enlarged view of the indicated area of detail shown in FIG. 13;

DETAILED DESCRIPTION

Figure 3:
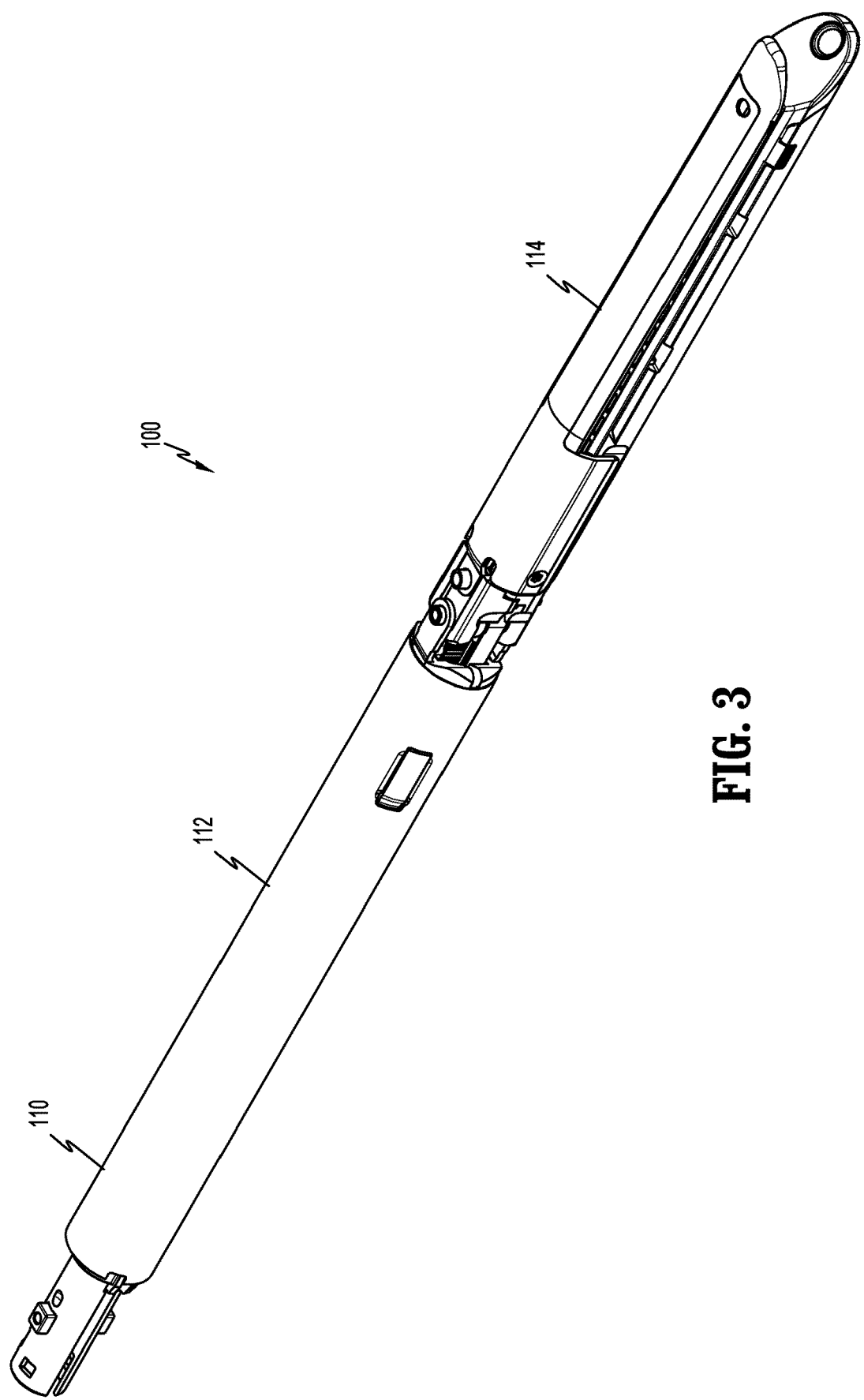
FIG. 3 is a side perspective view from the proximal end of a surgical stapler reload of the surgical stapler shown in FIGS. 1 and 2.

Aspects of the disclosed surgical stapler will now be described in detail with reference to the drawings wherein like reference numerals designate identical or corresponding elements in each of the several views. In this description, the term "proximal" is used generally to refer to the portion of the apparatus that is closer to a clinician, while the term "distal" is used generally to refer to the portion of the apparatus that is farther from the clinician. In addition, the term "endoscopic" procedure is used generally to refer to endoscopic, laparoscopic, arthroscopic, and any other surgical procedure performed through a small incision or a cannula inserted into a patient's body. Finally, the term "clinician" is used generally to refer to medical personnel including doctors, nurses, and support personnel.

The disclosed surgical stapler includes a tool assembly which supports a series of staples which are supported and configured to be ejected from a staple cartridge into an anvil to suture tissue.

FIG. 1 illustrates the disclosed surgical stapler 10, which includes a powered actuating device 12 having a handle assembly 12a, a body portion 14, which extends distally from the device 12, and a stapler reload 100 supported on a distal end of the body portion 14. The distal end of the body portion 14 is adapted to releasably engage a proximal end of the reload 100 such that actuation of the actuating device 12 effects operation of the reload 100. Although the actuating device 12 of the surgical stapler 10 of FIG. 1 is illustrated as a powered device, it is envisioned that the actuating device can also be configured for manual actuation. See, e.g., actuating device 12' in FIG. 2. Suitable actuating devices are disclosed in detail in U.S. Pat. No. 5,865,361 ("361 patent") and U.S. Pat. No. 7,143,924 ("924 patent"). Although the disclosed actuating devices are illustrated as powered and manually actuated handle assemblies, it is envisioned that other known actuating devices, including robotic devices, and different types of motorized devices, and/or electrically or mechanically driven devices, can be used to actuate the reload 100.

In alternate aspects of the disclosure, the reload 100 can be fixedly attached to the distal end of the handle assembly 12a and the surgical stapler 10 can be entirely disposable, or only a cartridge assembly of the reload 100 can be removable and replaceable. Alternatively, the reload 100 can be releasably coupled to the body portion 14 of the surgical stapler 10 and also have a removable and replaceable cartridge.

Figure 4:
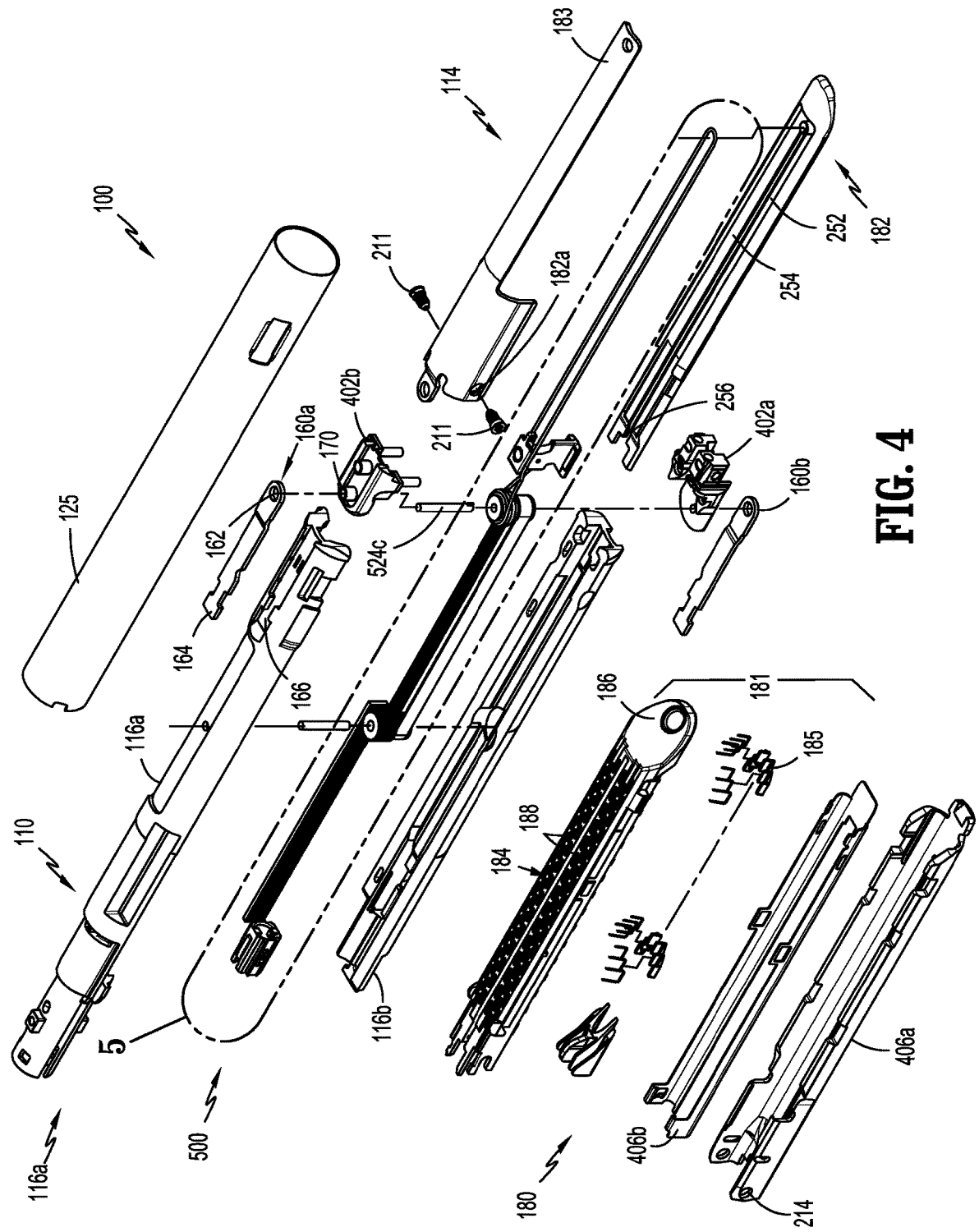
FIG. 4 is a side perspective, exploded view of the surgical stapler reload shown in FIG. 3.
Figure 7:
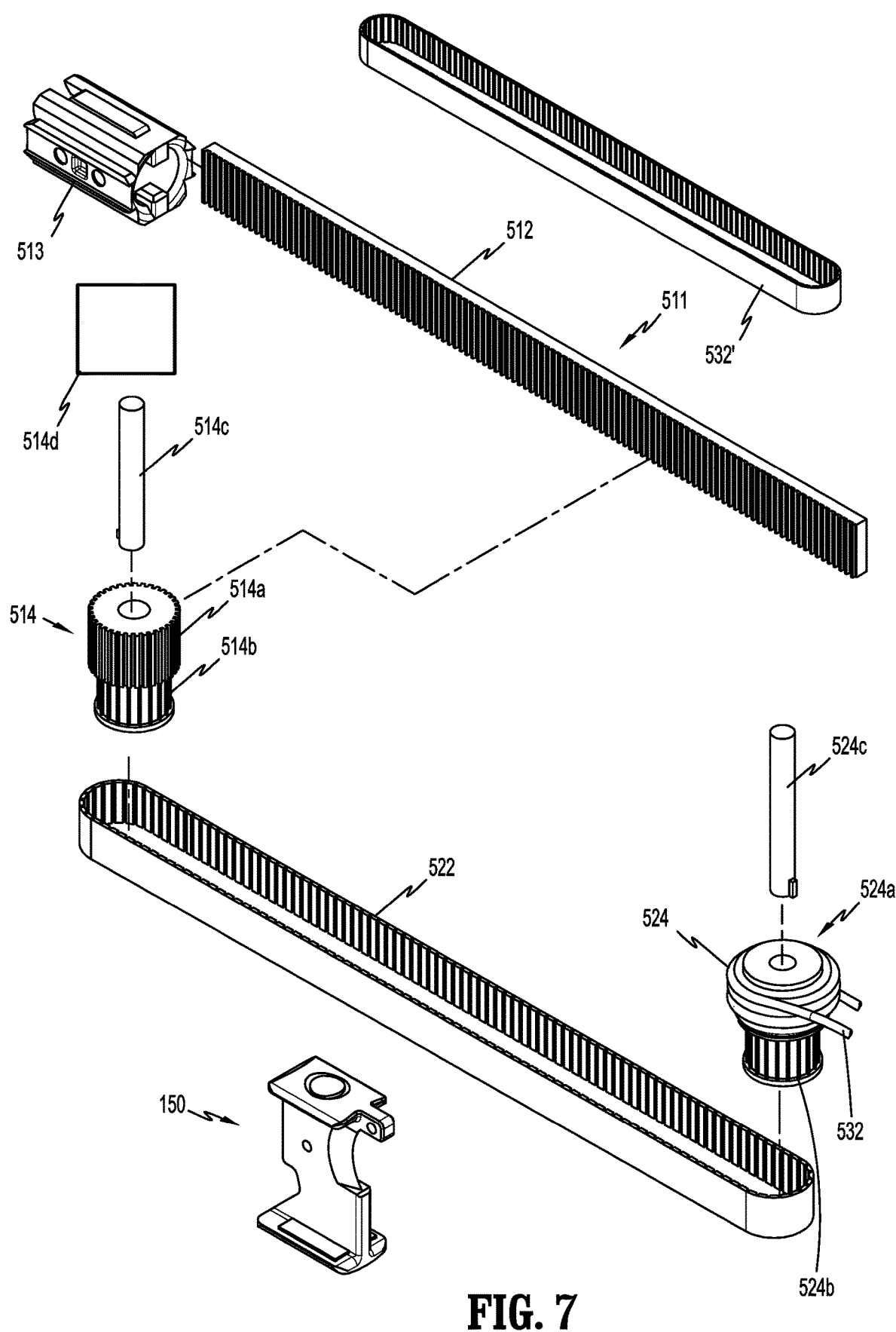
FIG. 7 is a side, perspective, exploded view of a drive train of the surgical stapler reload shown in FIG. 5.

Referring to FIGS. 3 and 4, the reload 100 includes a proximal body portion 110, an elongated shaft portion 112 defining a longitudinal axis "X" (FIG. 3), and a tool assembly 114. The proximal body portion 110 includes a drive assembly 500 (FIG. 4), and an inner housing 116 defined by an upper housing half-section 116a, and a lower housing half-section 116b. The housing half-sections 116a and 116b define channels which receive the drive assembly 500 as described in further detail below. The housing half-sections 116a and 116b are received within a tube 125 of the proximal body portion 110.

A pivot member 402a, 402b is secured to a distal end of the shaft housing half-sections 116a, 116b by upper and lower connecting members 160a, 160b. Each connecting member 160a, 160b includes a distal end which defines an opening 162 and a proximal end 164 which has a stepped configuration. The stepped configuration of the proximal end 164 of each connecting member 160a, 160b is received within a cutout 166 formed in the distal end of each of the upper and lower shaft housing half-sections 116a, 116b to axially fix the upper and lower connecting members 160a, 160b to the upper and lower shaft housing half-sections 116a, 116b, respectively. The openings 162 of each of the upper and lower connecting members 160a, 160b receive a respective pivot pin 170 formed on the upper and lower surfaces of the pivot member 402a, 402b to pivotally secure the pivot member 402a, 402b to the shaft housing half-sections 116a, 116b. A second pin 524c connects the pivot members 402a, 402b to each other and to the upper and lower connecting members 160a, 160b.

The tool assembly 114 includes a cartridge assembly 180, an opening 182a, and an anvil 182. The cartridge assembly 180 includes a staple cartridge 181 and a cartridge channel 406a. The staple cartridge 181 includes cartridge body 184, a cover 406b and a plurality of staples 185. The cartridge body 184 includes a tapered distal end 186 and first and second spaced legs 188 that are coupled together by the tapered distal end 186. The tapered distal end 186 of the cartridge body 184 functions as a tissue guide and directs tissue between the cartridge assembly 180 and anvil 182. Each of the first and second spaced legs 188 of the cartridge body 184 defines a plurality of staple pockets which are spaced along each leg 188 of the cartridge body 184. The opening 182a of the tool assembly 114 receives a pin 211 that extends through the opening 182a in a proximal end of the tool assembly 114 and through the opening 214 in the cartridge channel 406a.

Referring to FIGS. 4-6, the anvil 182 defines an elongated slot 252 and an elongated recess 254. The reload 100 includes an I-beam 150 (FIG. 6) that includes an upper beam 152, a lower beam 154, and a vertical strut 156. The vertical strut 156 of the I-beam 150 passes through the elongated slot 252 such that the upper beam 152 is slidably positioned in the elongated recess 254 of the anvil 182. A proximal end of the anvil 182 defines a tapered cam surface 256 which is positioned in engagement with a distal end of the upper beam 152 of the working I-beam 150 when the anvil 182 is in the open position (not shown). The lower beam 154 is positioned to move along the channel 406a of the cartridge assembly 180. The anvil 182 is biased to an open position by a biasing member, e.g., one or more leaf springs (not shown). In aspects of the disclosure, the leaf springs engage an undersurface of the anvil 182 to urge the anvil 182 away from the cartridge assembly 180 towards the open position.

Referring to FIGS. 5-9, the drive assembly 500 includes a proximal drive train 510 and a distal drive train 530 that is operatively coupled to the proximal drive train 510. The drive assembly 500 is configured to translate the I-beam 150 through the tool assembly 114 with the tool assembly 114 in an articulated or unarticulated position.

The proximal drive train 510 includes a coupling device 513, a rack assembly 511, and a proximal drive train linkage 522. The proximal drive train 510 is configured to translate motion from the coupling device 513 to the distal drive train 530. The distal drive train 530 is configured to translate the motion from the proximal drive train 510 to the I-beam 150. The coupling device 513 includes a proximal end and a distal end and supports a drive coupler (not shown) that is adapted to engage a control rod (not shown) of the actuating device 12 (FIG. 1) to operate the tool assembly 114 of the reload 100. coupling device The rack assembly 511 includes a rack gear 512 and a rotatable drive member 514. The rack gear 512 is disposed on the distal end of the coupling device 513 and is configured to translate longitudinal motion of the coupling device 513 into rotational movement of the rotatable drive member 514. More specifically, the rack gear 512 advances and/or retracts within the elongated shaft portion 112 of the reload 100 along the longitudinal axis "X" of the elongate shaft portion 112 in response to longitudinal movement of the coupling device 513. The rotatable drive member 514 is secured between the housing half-sections 116a, 116b about a first pin 514c (FIG. 7) and includes a pinion 514a and an idle roller 514b. The rack gear 512 engages the pinion 514a and imparts rotational motion to the pinion 514a as the rack gear 512 moves longitudinally within the elongated shaft portion 112 of the reload 100. Rotation of the pinion 514a imparts rotational motion to the idle roller 514b which is operably coupled to the proximal drive train linkage 522. The proximal drive train linkage 522 translates the rotational motion of the pinion 514a to the distal drive train 530. For example, inner teeth of the proximal drive train linkage 522 engage outer teeth on the pinion 514a. As the pinion 514a is rotated by the rack gear 512, the proximal drive train linkage 522 is advanced. In various aspects of the disclosure, the proximal drive train linkage 522 may be a wire, and/or a belt. In various aspects of the disclosure, the rack assembly 511 may include a motor 514d (FIG. 7) to drive the rotatable drive member 514.

Figure 10:
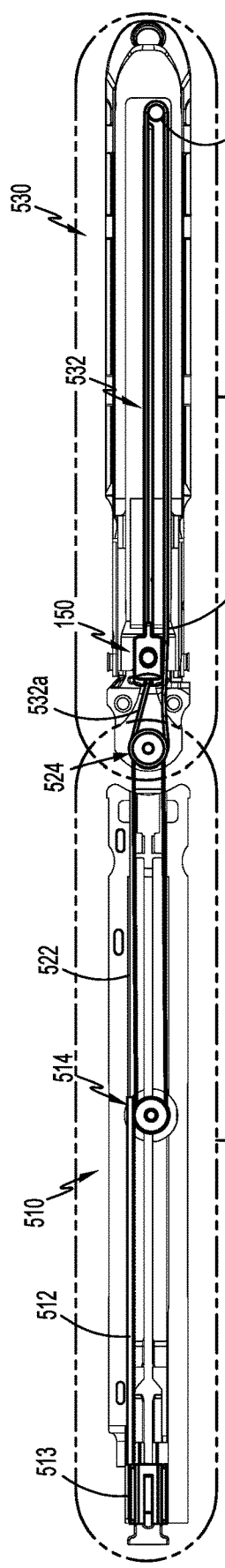
FIG. 10 is a top, functional view of the drive train of the surgical stapler reload shown in FIG. 1 with the tool assembly in a non-articulated, pre-fired position.

The distal drive train 530 is operatively coupled to the proximal drive train 510. The distal drive train 530 includes an active roller 524, a distal drive train linkage 532, and a roller 540 (FIG. 10). The distal drive train 530 is configured to translate the motion from the proximal drive train 510 to the I-beam 150. More specifically, the distal drive train 530 is coupled to the I-beam 150. The active roller 524 is secured to the proximal portion of the tool assembly 114 and is adapted to translate motion from the proximal drive train linkage 522 to the distal drive train linkage 532. The active roller 524 is secured to the proximal portion of the tool assembly 114 about a second pin 524c (FIG. 7) and includes a first portion 524b and a second portion 524a. The first portion 524b of the active roller 524 is operably coupled to the proximal drive train linkage 522. The second portion 524a of the active roller 524 is operably coupled to a second portion 532a (FIG. 15) of the distal drive train linkage 532. In various aspects of the disclosure, the distal drive train linkage 532 may include a metal or a synthetic wire, and/or a belt. For example, the first portion 532a of the distal drive train linkage 532 may be wrapped around the second portion 524a of the active roller 524 such that clockwise movement of the active roller 524 results in the advancement of the I-beam 150 through the tool assembly 114 and counter-clockwise movement of the active roller 524 results in retraction of the I-beam 150, or vice versa. A second portion 532b (FIG. 15) of the distal drive train linkage 532 is operably coupled to the roller 540. For example, the second portion 532b of the distal drive train linkage 532 may be wrapped around a portion of the roller 540. In various aspects of the disclosure, the roller may have a side surface the defines a depression configured to guide the second portion 532b of the distal drive train linkage 532 as it rotates around the roller 540. The roller 540 is disposed on the top surface of the anvil 182 (FIG. 4). In aspects, the distal drive train linkage 532' may include a belt. In other aspects, the distal drive train linkage 532 may include a pulley system.

In various aspects of the disclosure, the I-beam 150 (FIG. 6) includes a cutting edge 158 that is formed on or supported on a distal end of the vertical strut 156. The vertical strut 156 is slidably positioned in elongated slot 252, and between the legs 188 of the cartridge body 184, as described in further detail below. The I-beam 150 is positioned and configured to move through the tool assembly 114 when the distal drive train 530 is moved distally within the elongated shaft portion 112 to actuate the tool assembly 114. In certain aspects of the disclosure, the vertical strut 156 of the outer surface of the I-beam 150 includes a first cable attachment point 156a that is configured to be attached to the proximal end 532d of the distal drive train linkage 532. The upper face 157 of the outer surface of the I-beam 150 includes second cable attachment point 157a that is configured be attached to the distal end 532c of the distal drive train linkage 532.

Figure 11:
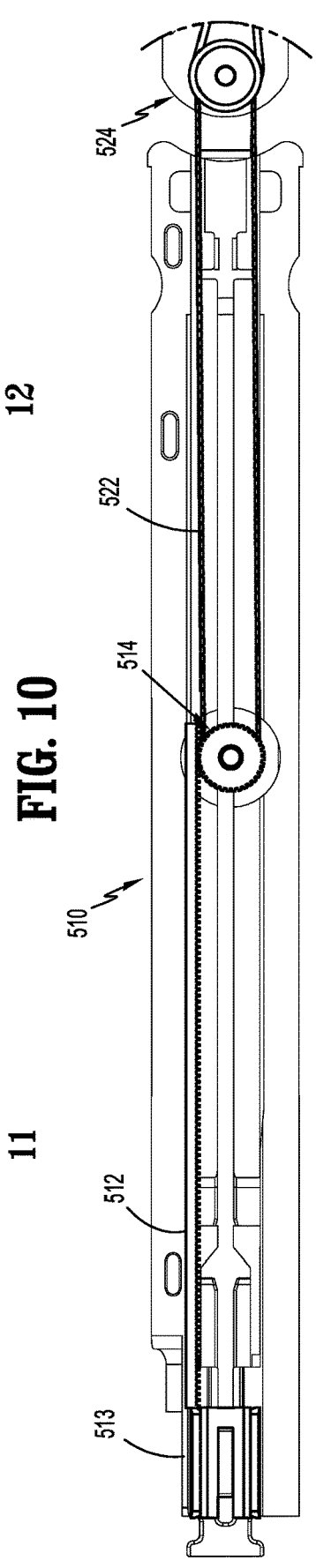
FIG. 11 is an enlarged view of the indicated area of detail shown in FIG. 10.
Figure 12:
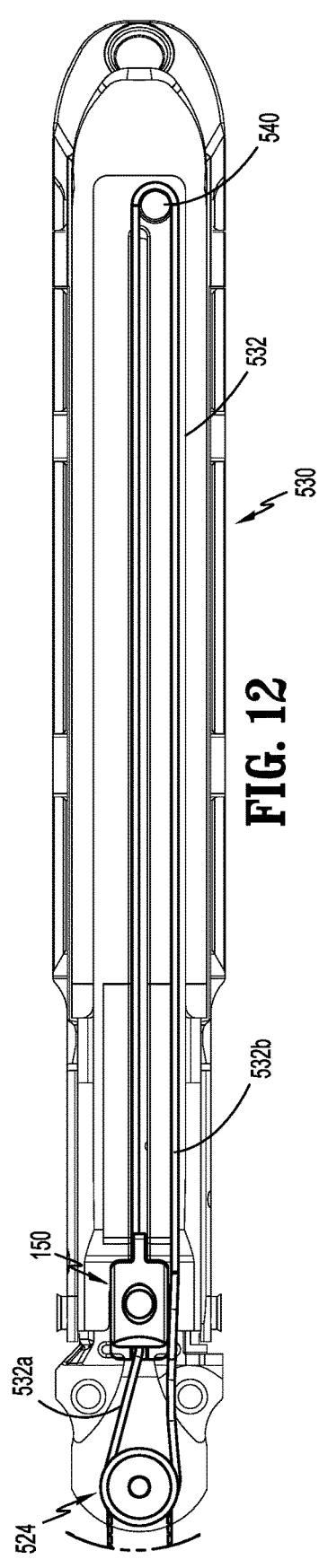
FIG. 12 is an enlarged view of the indicated area of detail shown in FIG. 10.

FIGS. 10-12 illustrate the reload 100 in a pre-fired non-articulated position in which the coupling device 513 of the proximal drive train 510 is in a first position, and the I-beam 150 is in a retracted position. FIGS. 13-15 illustrate the reload 100 in the non-articulated position as the reload 100 is fired. As the coupling device 513 is advanced, the rack assembly 511 is moved, causing the active roller 524 to rotate clockwise. The I-beam 150 moves forward as the active roller 524 rotates clockwise. In various aspects of the disclosure, the distal drive train linkage 532 may be comprised of a first portion 532a and a second portion 532b. As the first portion 532a is simultaneously wrapped around the second portion 524a of the active roller 524, the second portion 532b is unwrapped from around the active roller 524, causing a closed-loop pulling the I-beam 150 forward into a fired position. As the coupling device 513 is advanced distally within the elongated shaft portion 112, the rack gear 512 advances and/or retracts within the elongated shaft portion 112 of the reload 100 along the longitudinal axis "X" of the elongate shaft portion 112. The rack gear 512 rotatably engages the rotatable drive member 514 and rotates the rotatable drive member 514. When the rotatable drive member 514 is rotated, the proximal drive train linkage 522 rotates about the first portion 524b to rotate the active roller 524. The active roller 524 engages the distal drive train linkage 532 which rotates about the active roller 524 to longitudinally drive the I-beam 150 forward and/or back.

With reference to FIG. 13, the coupling device 513 of the proximal drive train 510 is in a second position, and the I-beam 150 is in the fired position. With reference to FIGS. 10-12, as the coupling device 513 of the proximal drive train 510 is retracted, it pulls the rack assembly 511 proximally, rotating the active roller 524 counterclockwise. The I-beam 150 moves backward as the active roller 524 rotates counterclockwise. As the first wire is simultaneously unwrapped from around the second portion 524a of the active roller 524, the second wire is wrapped around the active roller 524, causing a closed-loop pulling the I-beam 150 to a retracted position.

Figure 16:
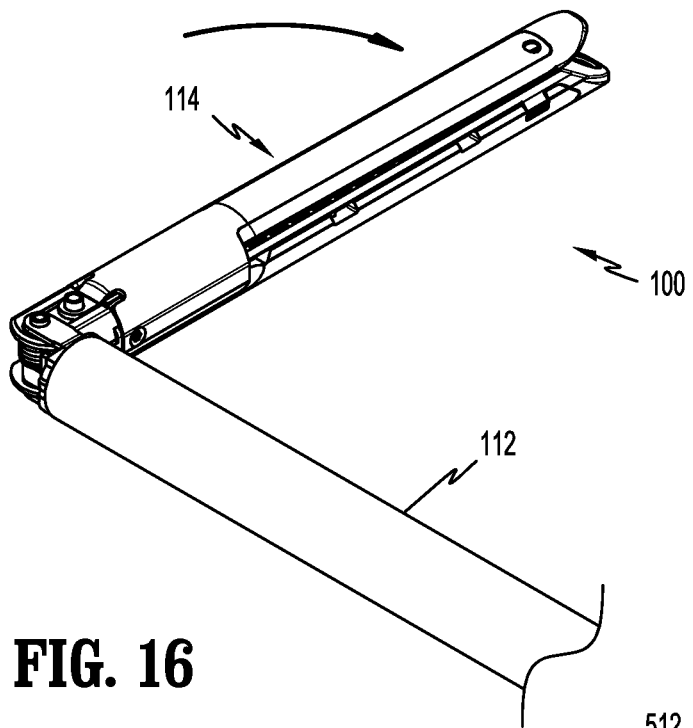
FIG. 16 is a side, perspective view of the drive train of the surgical stapler reload shown in FIG. 5 in the articulated and fired position.
Figure 17:
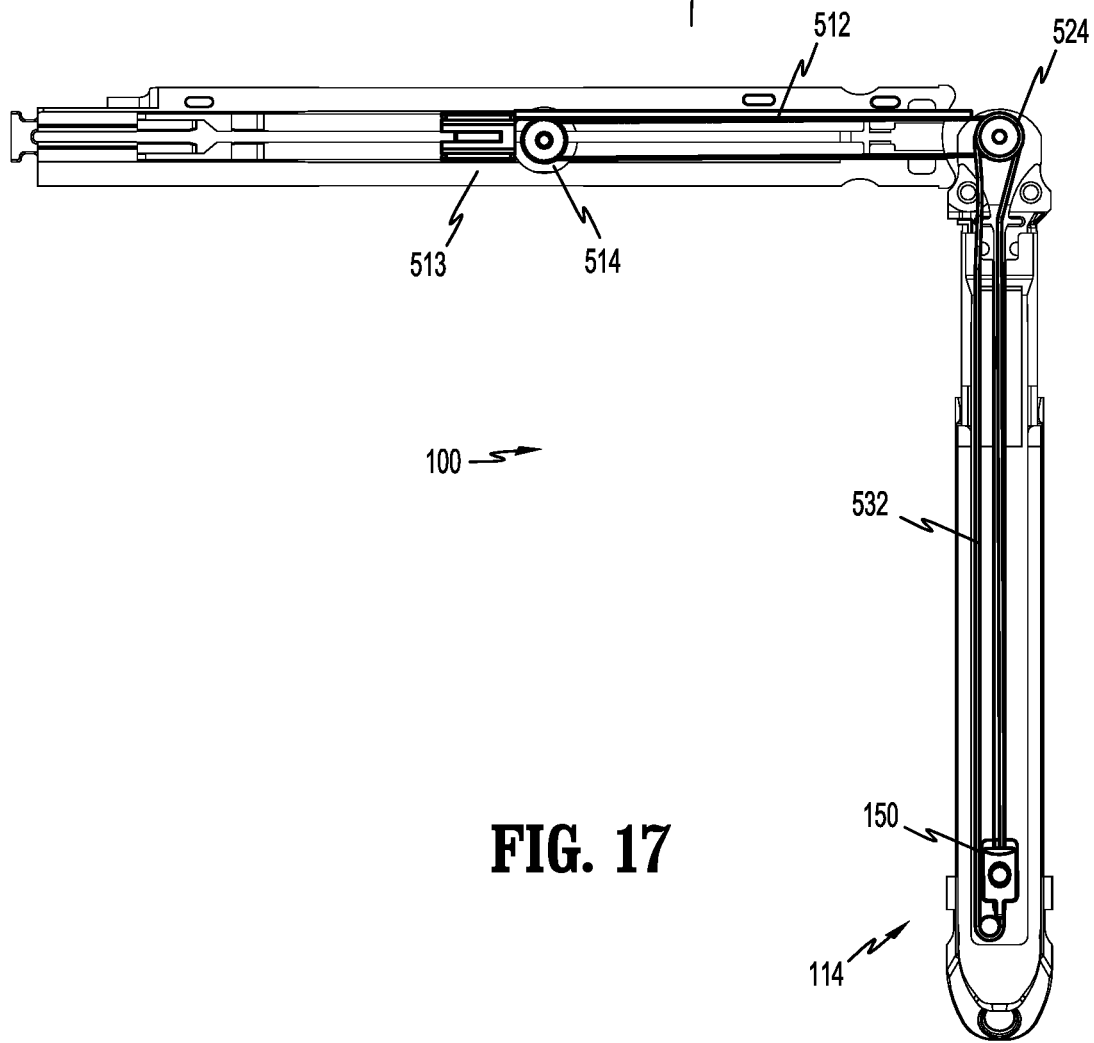
FIG. 17 is a top, functional view of the drive train of the surgical stapler reload shown in FIG. 5 in the articulated and fired position.

With reference to FIGS. 15 and 16, a functional view of the reload 100 articulated at 90 degrees is shown. As illustrated, the coupling device 513 of the proximal drive train 510 is in the second position and has advanced the rack gear 512 which is disposed on the distal end of the coupling device 513. The rack gear 512 which is rotatably engaged with the pinion 514a and has imparted clockwise rotational motion to the pinion 514a. The pinion 514a which is engaged with the proximal drive train linkage 522, has imparted rotational motion to the active roller 524 to advance the distal drive train linkage 532 and advance the I-beam 150 to a fired or advanced position within the cartridge body 184. In various aspects of the disclosure, the reload 100 may be articulated to any angle between 0 and +/−90 degrees.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A drive assembly comprising:
   a proximal drive train including:
      a rotatable drive member defining a transverse axis, the rotatable drive member including:
         a pinion engaged by a longitudinally movable rack gear; and
         an idle roller; and
      a proximal drive train linkage defining a first longitudinal axis and having a first portion and a second portion, the first portion of the proximal drive train linkage operably coupled to the idle roller of the rotatable drive member, the proximal drive train linkage including a belt; and
   a distal drive train including:
      an active roller operably coupled to the second portion of the proximal drive train linkage;
      a distal drive train linkage defining a second longitudinal axis and including a wire, the distal drive train linkage having a first portion and a second portion, the first portion of the distal drive train linkage coupled to the active roller;
      a guide roller engaged with the second portion of the distal drive train linkage; and
      an I-beam operably coupled to the distal drive train linkage, the I-beam configured to be advanced along the second longitudinal axis of the distal drive train linkage in response to rotational motion of the rotatable drive member.

2. The drive assembly of claim 1, wherein the rotatable drive member is driven by a motor.

3. The drive assembly of claim 1,
   wherein longitudinal movement of the rack gear imparts rotational motion to the pinion.

4. The drive assembly of claim 3, wherein the rack gear is coupled to a coupling device, such that longitudinal movement of the coupling device imparts longitudinal movement to the rack gear.

5. The drive assembly of claim 4, wherein the pinion is coupled to the proximal drive train linkage.

6. The drive assembly of claim 5, wherein the distal drive train linkage is configured to advance or retract the I-beam.

7. The drive assembly of claim 1, wherein the distal drive train linkage includes a pulley system.

8. The drive assembly of claim 1, wherein the wire includes at least one of a metal wire or a synthetic wire.

9. The drive assembly of claim 1, wherein the drive assembly is configured for enabling articulation of a reload of a surgical instrument to any angle between 0 and +/−90 degrees.

10. A surgical reload assembly comprising:
    a tool assembly defining a first longitudinal axis, the tool assembly including an anvil and a cartridge assembly, the cartridge assembly including a staple cartridge supporting a plurality of staples; and
    a drive assembly configured to eject staples from the surgical reload assembly, the drive assembly including:
       a proximal drive train including:
          a rotatable drive member defining a transverse axis, the rotatable drive member including:
             a pinion engaged by a longitudinally movable rack gear; and an idle roller; and
   a proximal drive train linkage operably coupled to the rotatable drive member, the proximal drive train linkage is operably coupled to the idle roller, the proximal drive train linkage defining a longitudinal axis, wherein the proximal drive train linkage includes a belt; and
a distal drive train operably coupled to the proximal drive train, the distal drive train including:
   an active roller operably coupled to the proximal drive train linkage;
   a distal drive train linkage defining a second longitudinal axis, wherein the distal drive train linkage includes a wire;
   a roller including a side surface that defines a depression configured to guide a portion of the distal drive train linkage; and
   an I-beam operably coupled to the distal drive train linkage, wherein the I-beam is configured to be advanced along the second longitudinal axis in response to rotational motion of the rotatable drive member through the tool assembly to eject the plurality of staples from the staple cartridge.

11. The surgical reload assembly of claim 10, wherein the rotatable drive member is configured to be driven by a motor.

12. The surgical reload assembly of claim 10, wherein longitudinal movement of the rack gear imparts rotational motion to the pinion.

13. The surgical reload assembly of claim 12, wherein the rack gear is configured to be operably coupled to a coupling device, such that longitudinal movement of the coupling device imparts longitudinal movement of the rack gear.

14. The surgical reload assembly of claim 13, wherein the pinion is coupled to the proximal drive train linkage.

15. The surgical reload assembly of claim 14, wherein the distal drive train linkage advances or retracts the I-beam.

16. The surgical reload assembly of claim 10, wherein the distal drive train linkage includes a pulley system.

17. The surgical reload assembly of claim 10, wherein the wire includes at least one of a metal wire or a synthetic wire.

* * * * *